United States Patent

Parthasarathi et al.

[11] Patent Number: 5,974,885
[45] Date of Patent: Nov. 2, 1999

[54] METHOD AND APPARATUS FOR MEASURING SILVER SHEATH THICKNESS DURING DRAWING OF HIGH TEMPERATURE SUPERCONDUCTING WIRE

[75] Inventors: Sanjai Parthasarathi, Santa Clara, Calif.; Michael D Aesoph, Johnstown; Jan Kajuch, Windber, both of Pa.

[73] Assignee: Concurrent Technologies Corporation, Johnstown, Pa.

[21] Appl. No.: 08/852,839

[22] Filed: May 7, 1997

Related U.S. Application Data

[60] Provisional application No. 60/034,416, Jan. 6, 1997.

[51] Int. Cl.$^6$ .................................................. G01N 29/24
[52] U.S. Cl. .................................. 73/597; 73/622; 73/629
[58] Field of Search .............................. 73/597, 600, 622, 73/159, 629; 72/31.13

[56] References Cited

U.S. PATENT DOCUMENTS

| | | |
|---|---|---|
| H1084 | 8/1992 | Bylenok et al. . |
| 3,678,737 | 7/1972 | Miller . |
| 3,916,676 | 11/1975 | Boggs et al. ............................... 73/622 |
| 4,008,602 | 2/1977 | Love . |
| 4,196,607 | 4/1980 | Youtsey et al. . |
| 4,918,989 | 4/1990 | Desruelles et al. . |
| 4,976,148 | 12/1990 | Migliori et al. . |
| 4,991,440 | 2/1991 | Pleinis et al. . |
| 5,009,103 | 4/1991 | Sato et al. . |
| 5,029,476 | 7/1991 | Metala et al. . |
| 5,056,368 | 10/1991 | Kawasaki et al. . |
| 5,062,300 | 11/1991 | Vallee . |
| 5,063,780 | 11/1991 | Landry et al. . |
| 5,168,469 | 12/1992 | Liberto et al. . |
| 5,182,139 | 1/1993 | Frankel et al. . |
| 5,271,275 | 12/1993 | La Force ................................... 73/622 |

FOREIGN PATENT DOCUMENTS

| | | |
|---|---|---|
| 92 409 | 7/1981 | Japan . |
| 97 404 | 6/1982 | Japan . |
| 125809 | 8/1982 | Japan . |
| 191508 | 11/1982 | Japan . |
| 46 407 | 3/1985 | Japan . |

Primary Examiner—Hezron Williams
Assistant Examiner—Helen C. Kwok
Attorney, Agent, or Firm—Draughon P.A.; Mark J. Young; C. Joan Gilsdorf

[57] ABSTRACT

An ultrasonic method to measure silver sheath thickness in silver sheathed, ceramic powder core High Temperature Superconductor (HTS) wires and an associated sensor system which is designed and developed for continuous, on-line, real-time measurement during wire drawing.

23 Claims, 8 Drawing Sheets

METHOD AND APPARATUS FOR MEASURING SILVER SHEATH THICKNESS DURING DRAWING OF HIGH TEMPERATURE SUPERCONDUCTING WIRE

This application claims benefit of provisional application Ser. No. 60/034,416 filed Jan. 6, 1997.

GOVERNMENT RIGHTS

The U.S. Government has a paid-up license in this invention and the right in limited circumstances to require the patent owner to license others on reasonable terms as provided for by the terms of Contract No. N00140-92-C-BC49 awarded by the U.S. Navy.

BACKGROUND

Since the discovery of high temperature superconducting bismuth-based oxides in the late 1980's, there has been a frenzy of development aimed at manufacturing long lengths of wires and tapes for use in practical superconducting magnets. Currently, the ceramic powder in silver tube process, or more commonly known as Powder-In-Tube (PIT) method, is the only process capable of fabricating long length (more than 10 meters), mechanically robust High Temperature Superconductors (HTS) with good superconducting properties. In the PIT method, superconducting ceramic powders are loaded into a silver tube which is then mechanically worked utilizing extrusion, drawing, swaging, and rolling to produce long wires or tapes. A final heat treatment produces the superconducting phase. The PIT process has been, and continues to be, developed by trial and error, a time-consuming and expensive process. There is an urgent need for improved process quality management and control of PIT HTS manufacturing which would minimize the trial and error.

The development of advanced sensing techniques for process quality control throughout the various stages of HTS wire manufacturing promises to reduce manufacturing costs and enhance HTS wire quality. Uniformity of conductor dimensions and ceramic core density are of critical importance to the in-service performance of HTS wire. All current applications of HTS wire are basically static in nature, such as the large magnets in Magnetic Resonance Imaging (MRI) systems. The consequences of failure in these applications are relatively low. In the next generation of HTS wire implementation, the emphasis will be on dynamic, high stress applications such as transportation, power generation and storage where the consequences of failure are substantial. Process quality management will become a prerequisite to HTS wire implementation in these critical applications.

The silver sheath of silver sheathed ceramic powder core HTS wire significantly affects the mechanical properties of the HTS wire in several ways. First, silver sheathed tapes (obtained by rolling the wire) have proven to exhibit the highest critical current density (Jc) among all HTS products except for thin films. Second, the silver sheath is substantially inert and allows the penetration of oxygen during the heat treatment process and does not "poison" the superconductor. Third, the silver sheath provides mechanical strength and integrity to the wire. Its ductility helps in winding the wire to produce useful magnets (otherwise impossible to make out of a brittle ceramic material).

Given the importance of the silver sheath, its dimensional uniformity (implying a uniform ceramic core) is critical to the electrical performance characteristics of the HTS wire. For example, the non-uniformity of the ceramic core often results in a critical defect called sausaging. Sausaging defects typically occur during the last stages of the PIT process and results in a significant decrease in critical current density (Jc).

Consequently, the measurement of silver sheath thickness is important from both process development and in-process monitoring standpoints. Current quality control practices to measure silver sheath thickness in HTS wire employ destructive metallographic characterization techniques. These techniques involve careful sectioning, mounting and evaluation under an optical microscope. These techniques are destructive, inherently time consuming and cannot be used on routine evaluation on production wire. In this context, a sensor for continuous measurement of silver sheath thickness during wire fabrication offers considerable advantages. Presently, such sensors to measure sheath thickness in composite HITS wire do not exist. The development of a nondestructive technique and an associated sensor for real-time measurement during HTS wire drawing promises significant benefits.

Ultrasonic techniques have been shown capable of thickness measurements in a variety of applications. In this technique, the time of flight of an ultrasonic pulse in a material is used to determine thickness, assuming that the velocity of the pulse in the material is known. Ultrasonic techniques are non destructive, rapid and can be automated for real-time, continuous monitoring of HTS wire manufacturing. However, a sensor to measure silver sheath thickness in HTS wire based on such ultrasonic techniques has not been previously developed.

SUMMARY

It is among the objects of the present invention to provide a method to measure silver sheath thickness in silver sheathed, ceramic powder core HTS wires and an associated sensor system which is designed and developed for continuous, on-line, real-time measurement during wire drawing. The time taken for a high frequency ultrasonic pulse to propagate through the silver sheath, get reflected at the sheath/ceramic interface and arrive back at the transducer is measured (time of flight). The ultrasonic transducer is housed in a specially developed fixture to enable measurements on moving wire. From the time of flight measurement and the ultrasonic wave velocity in silver, the sheath thickness can be determined and monitored with the aid of a computer. The sensor is non-destructive, rapid and is automated for real-time, continuous measurement of sheath thickness during HTS wire manufacturing.

DESCRIPTION

Figure 1:
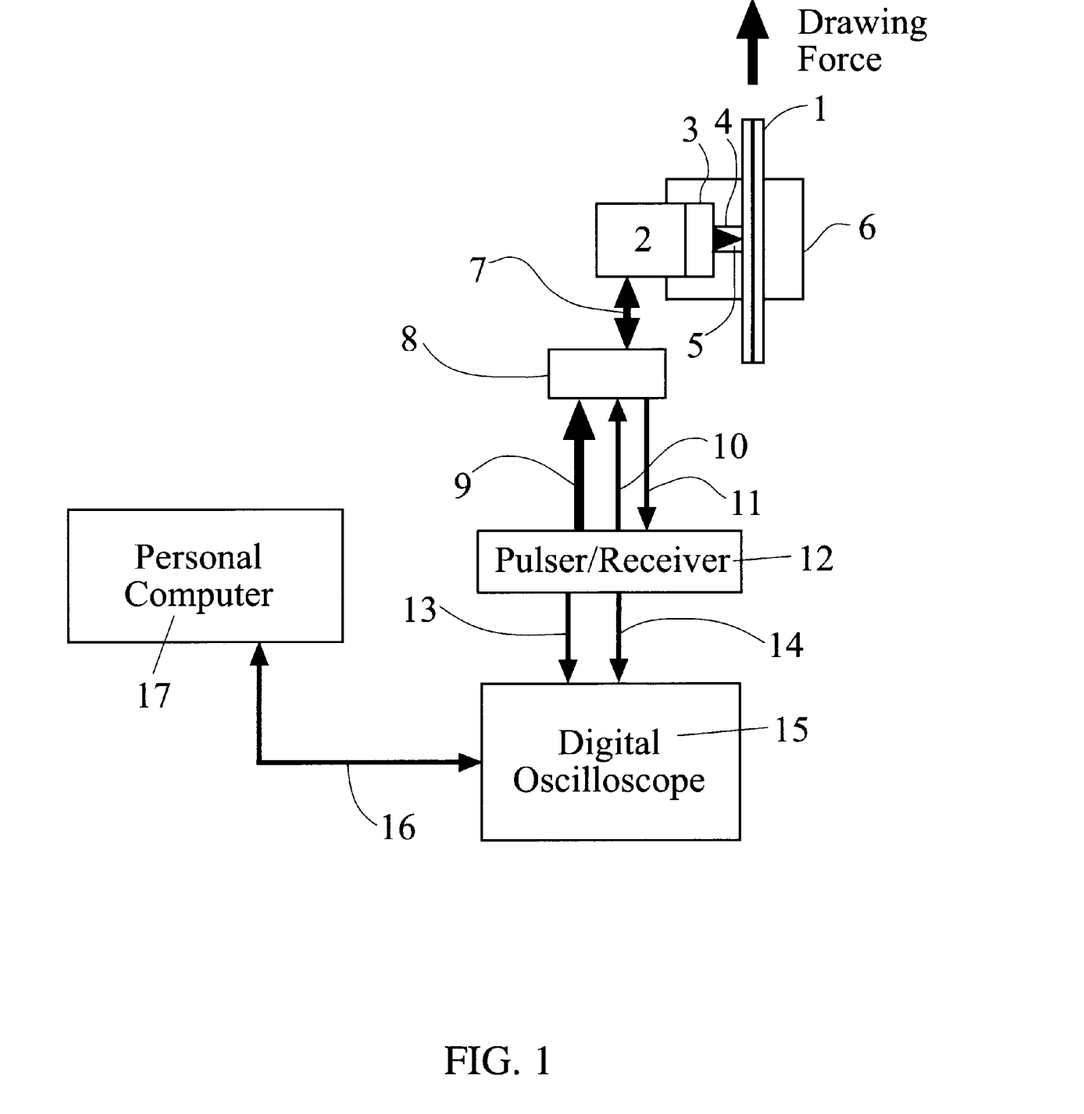
FIG. 1 is an overview of the ultrasonic sensor system.

The sensor system can be constructed in any number of ways. However, only the best mode will be described. The overall sensor system is shown in FIG. 1. The HTS wire 1 is routed through a wire drawing fixture 6 that positions the HTS wire 1 for ultrasonic measurements. The ultrasonic transducer 2 and the squirter assembly 3 are mounted sideways on the wire drawing fixture 6. The wire drawing fixture 6 allows for the accurate placement of the HTS wire 1 in relation to a high frequency (50 MHz) ultrasonic transducer 2 and squirter assembly 3. The focused ultrasonic energy pulse 5 is transmitted via a water stream 4 to the HTS wire 1, and is reflected back to the ultrasonic transducer 2 as a reflected ultrasonic energy signal 34, 35, 36.

To reduce cable reflections, the remote pulser preamp 8 is connected with a short pulser cable 7 to the ultrasonic transducer 2. The pulser preamp 8 is supplied with a continuous power supply 9 to provide a pulse energy for ultrasonic transducer 2 excitation. The ultrasonic transducer 2 is pulsed via the pulser cable 7 when the remote pulser preamp 8 is triggered by the pulser/receiver 12 using the remote trigger line 10. The ultrasonic energy signal travels through the signal line 11 and is amplified by the pulser receiver 12 and an amplified ultrasonic energy signal is transmitted by the signal out line 13 to the digital oscilloscope 15 where it is digitized into a digital ultrasonic energy signal.

The digital oscilloscope 15 is triggered by the pulser/receiver 12 through the external trigger line 14. The digital oscilloscope 15 acquires and digitizes the ultrasonic energy signal from the pulser/receiver 12 through the signal out line 13. The digital ultrasonic energy signal is transferred via a General Purpose Interface Bus (GPIB) 16 to a digital computer 17 for analysis.

Figure 2:
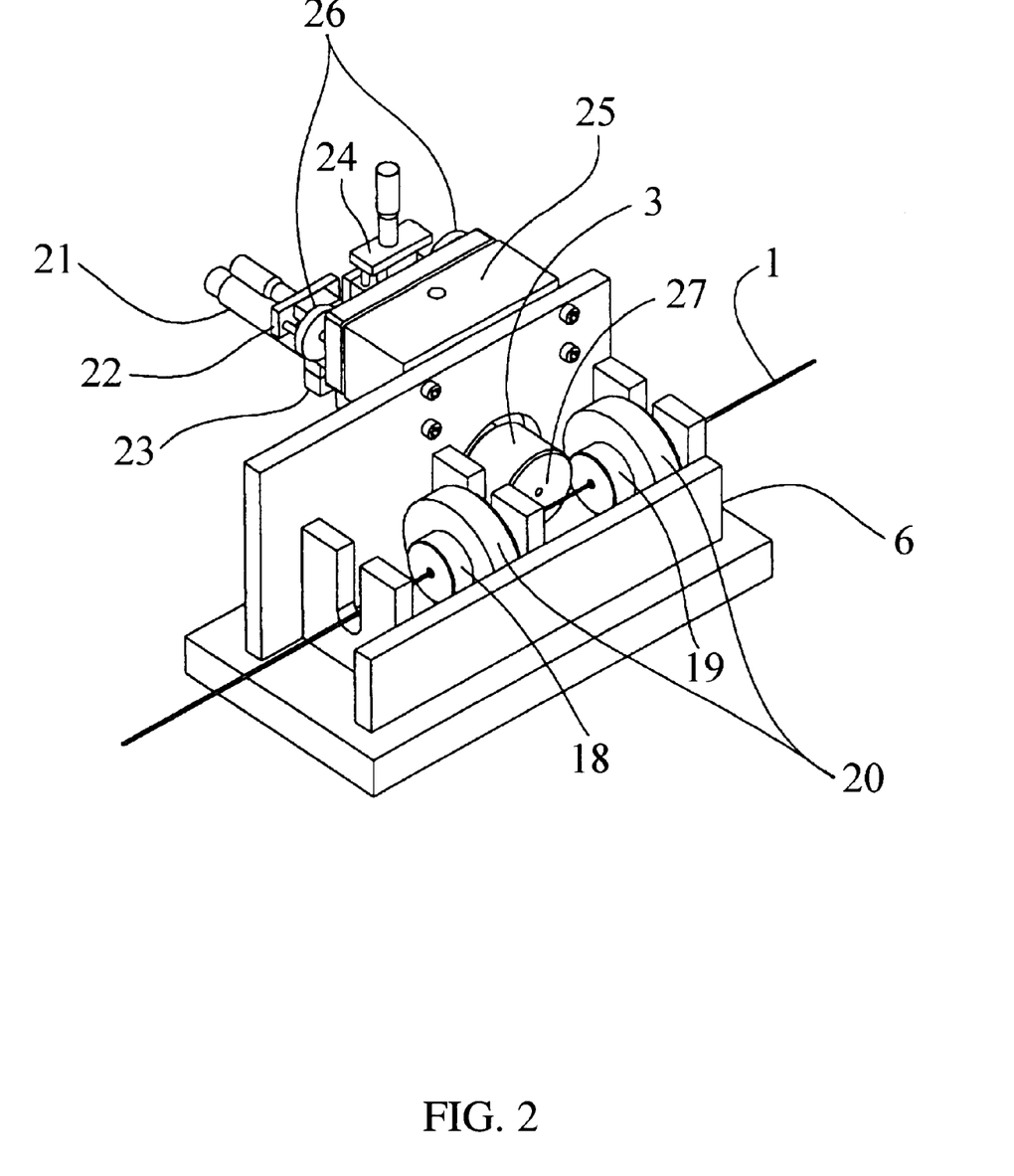
FIG. 2 is a downstream view of the wire drawing fixture.
Figure 3:
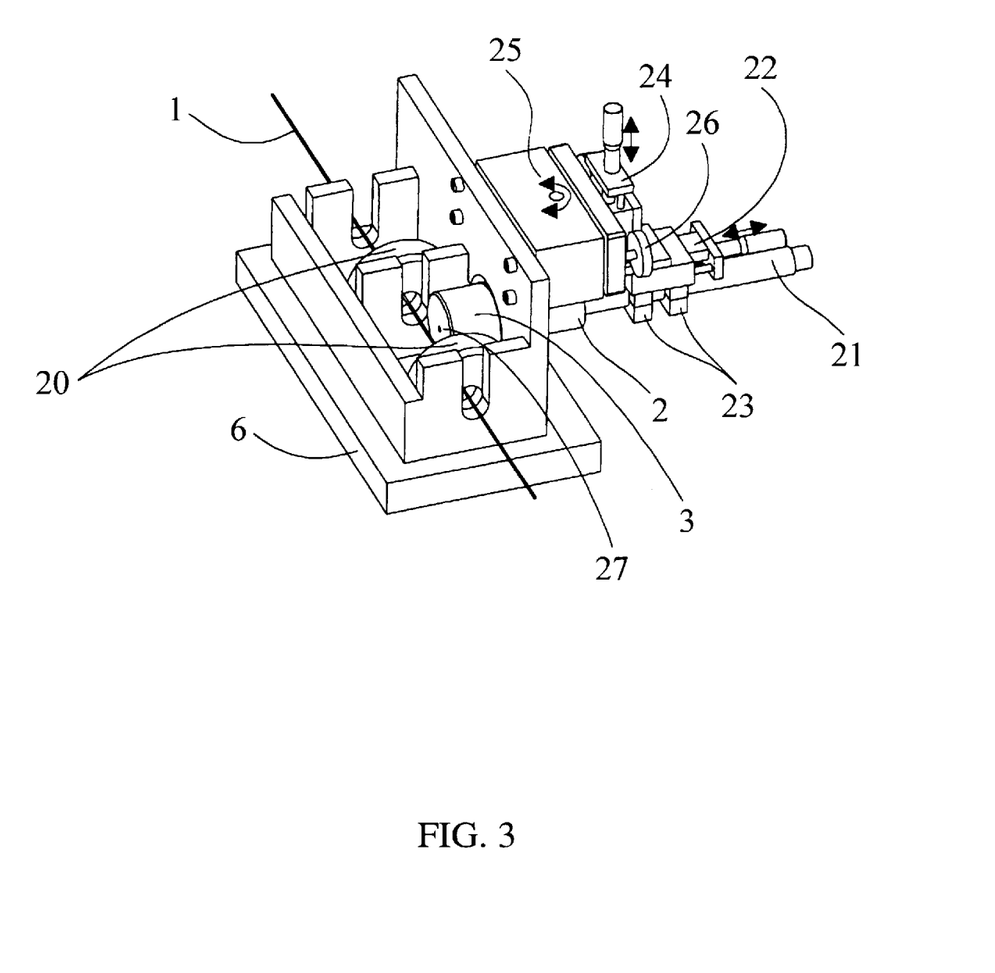
FIG. 3 is an upstream view of the wire drawing fixture.
Figure 4:
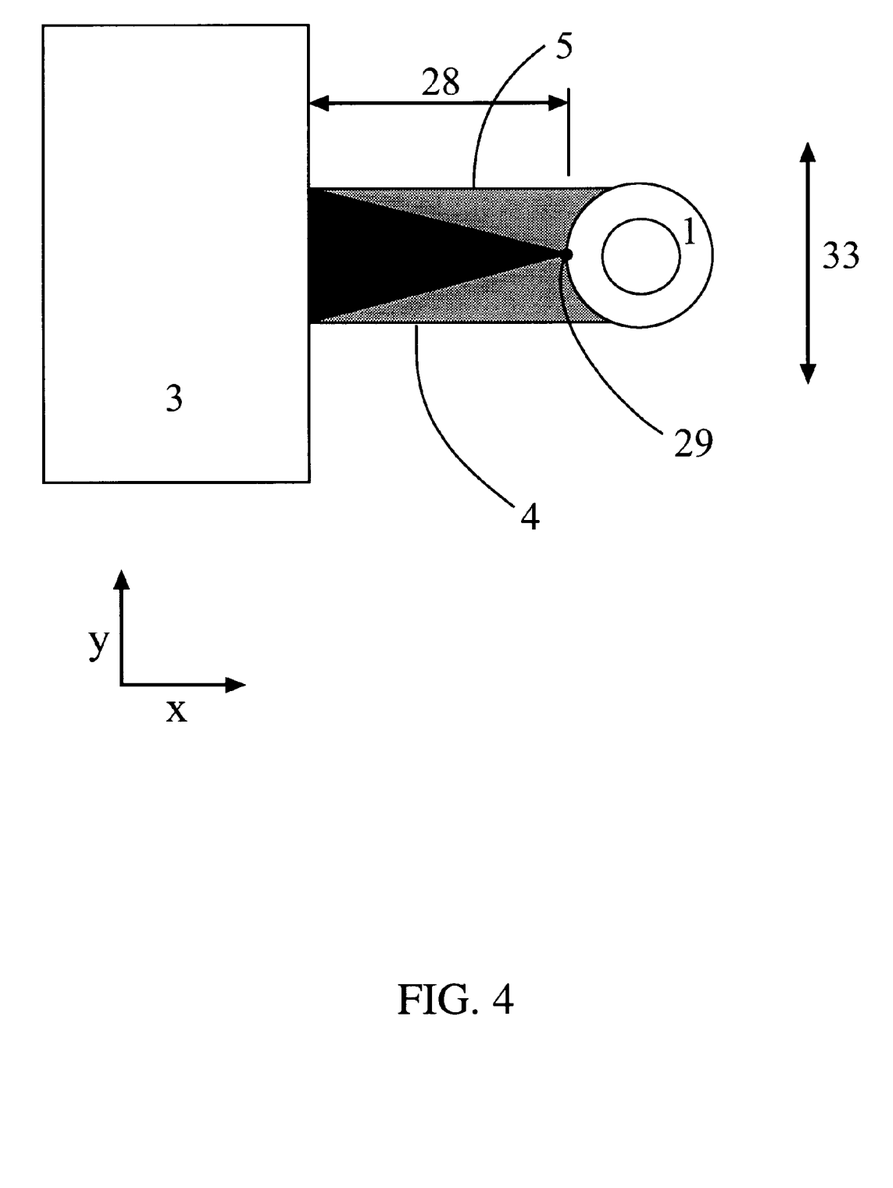
FIG. 4 is a schematic of the standoff and vertical ultrasonic transducer adjustments.
Figure 5:
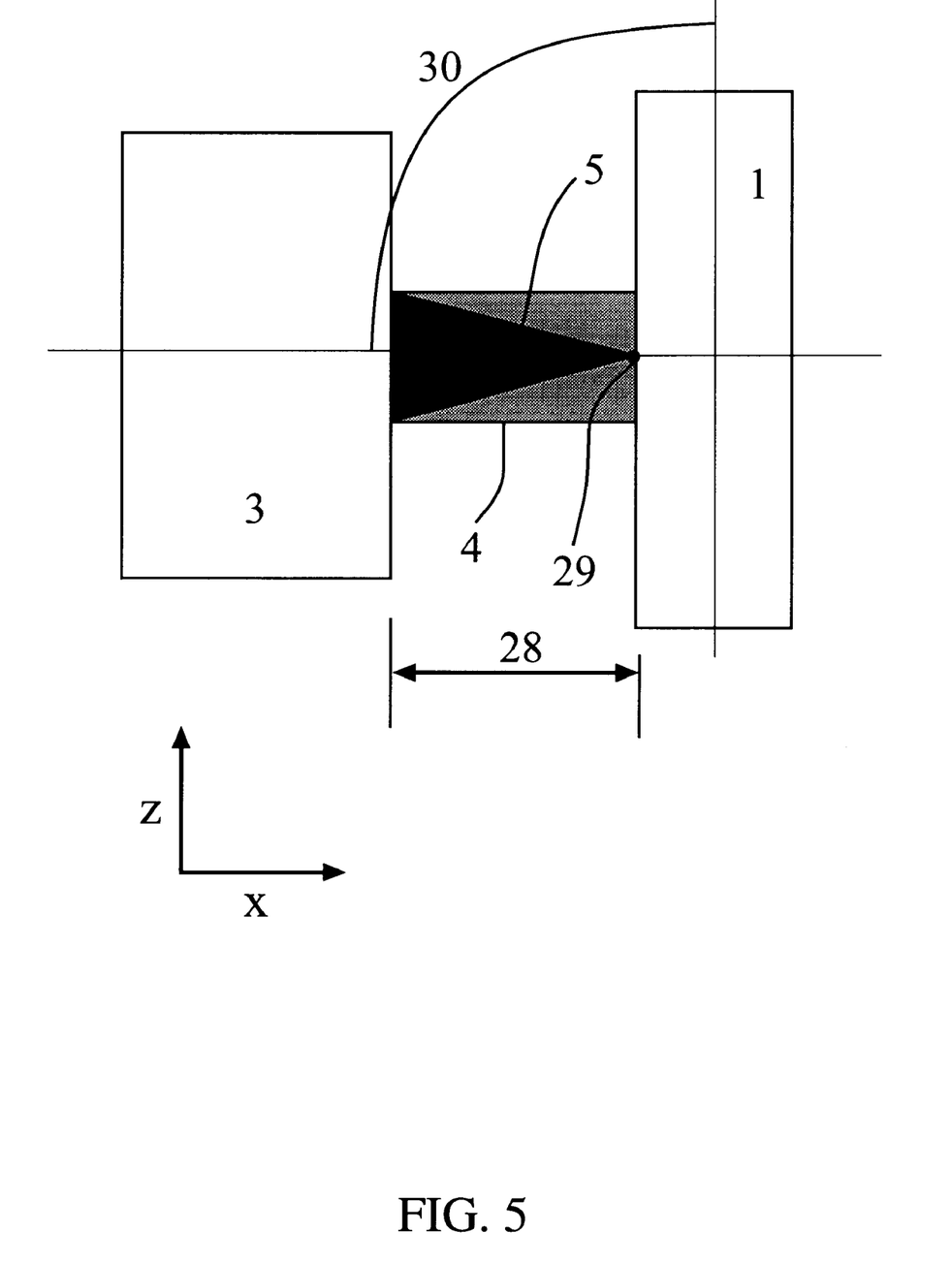
FIG. 5 is a schematic of the standoff and angular ultrasonic transducer adjustments.

As shown in FIGS. 2 and 3, the HTS wire 1 is routed through the wire drawing fixture 6 during the wire drawing process. The wire drawing fixture 6 consists of the drawing die 18, guide die 19, the die mounting blocks 20, the ultrasonic transducer 2, the squirter assembly 3, and the associated hardware to accurately locate the focal point of the ultrasonic energy 5. The guide die 19 is the same diameter as the drawing die 18 and is used to stabilize the wire for measurement during drawing. The ultrasonic transducer 2 is fitted with a squirter assembly 3 which emits a stream of liquid via a liquid jet hole 27 in the liquid filled chamber 41 of the assembly to allow for the transfer of ultrasonic energy 5 from the ultrasonic transducer 2 to the HTS wire 1. The ultrasonic transducer 2 is mounted on an ultrasonic tube 21 which is mounted to the axial stage 22 by four mounting blocks 23. The axial stage 22 is mounted on the vertical stage 24, which is mounted on the angular adjustment fixture 25 to provide for all the adjustments required to obtain a usable signal. The adjustments allow for three degrees of freedom for the ultrasonic transducer 2 (see FIGS. 4 and 5): vertical positioning 33 (as depicted in FIG. 4), standoff positioning 28 (as depicted in FIGS. 4 and 5) and angular positioning 30 (as depicted in FIG. 5). The vertical positioning 33 (as depicted in FIG. 4) is accomplished by adjusting the vertical stage 24. The standoff positioning 28 (as depicted in FIGS. 4 and 5) is set by adjusting the axial stage 22. The angular positioning 30 (as depicted in FIG. 5) is accomplished by adjusting the angular positioning fixture 25 by turning both angular adjustment knobs 26.

Referring to FIG. 4, the vertical positioning 33 and standoff positioning 28 of the ultrasonic transducer 2 (as depicted in FIG. 3) and squirter assembly 3 are adjusted such the focal point 29 of the focused ultrasonic energy 5 is positioned on the surface of the HTS wire 1 in a plane normal to the centerline.

Referring to FIG. 5, the incidence angle (angular positioning 30) of the ultrasonic energy 5, standoff positioning 28 of the ultrasonic transducer 2 (as depicted in FIG. 3) and squirter assembly 3 are adjusted such that the focal point 29 of the focused ultrasonic energy 5 is positioned on the surface of the HTS wire 1 in a plane normal to the centerline.

Figure 6:
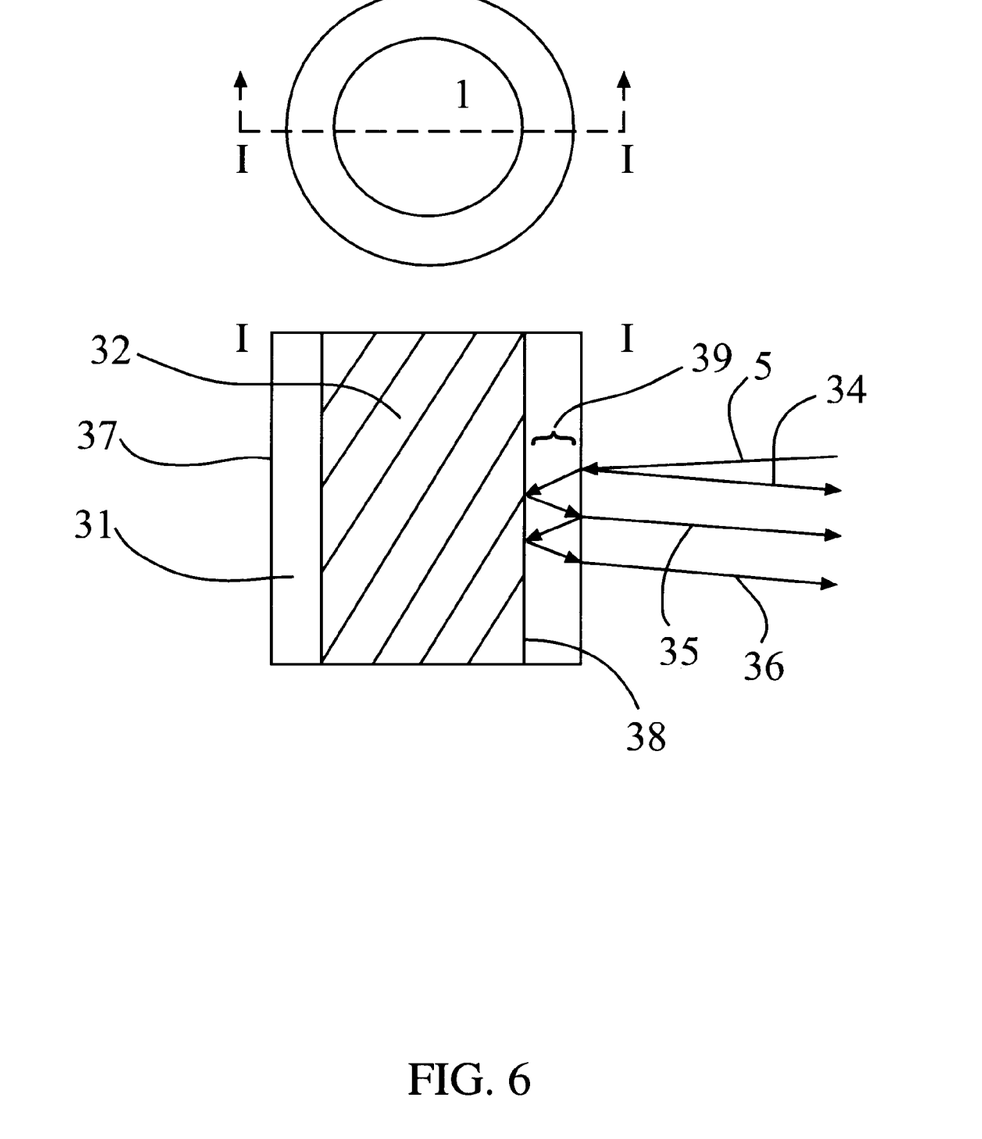
FIG. 6 is a sectional view of a composite HTS wire showing the ultrasonic signal paths.

A section of HTS wire 1 and its cross section is shown in FIG. 6. The HTS wire 1 is a composite wire consisting of a silver sheath 31 surrounding a ceramic core 32. The path 34–36 of the ultrasonic energy 5, generated by an ultrasonic transducer 2, (as depicted in FIG. 3) is also shown in FIG. 6. The impingent ultrasonic energy 5 is focused on the silver sheath surface 37 to provide for the maximum energy transfer into the silver sheath 31. Some of this energy is reflected 34 at the water/silver sheath surface 37 interface and returns to the ultrasonic transducer 2 (as depicted in FIG. 3). The remaining ultrasonic energy 5 propagates through the silver sheath 31 and is reflected between the silver/core 38 interface and the water/silver sheath surface 37 interface and ultimately returns to the ultrasonic transducer 2 (as depicted in FIG. 3) via a first 35 and a second 36 silver/core interface signal.

Figure 7:
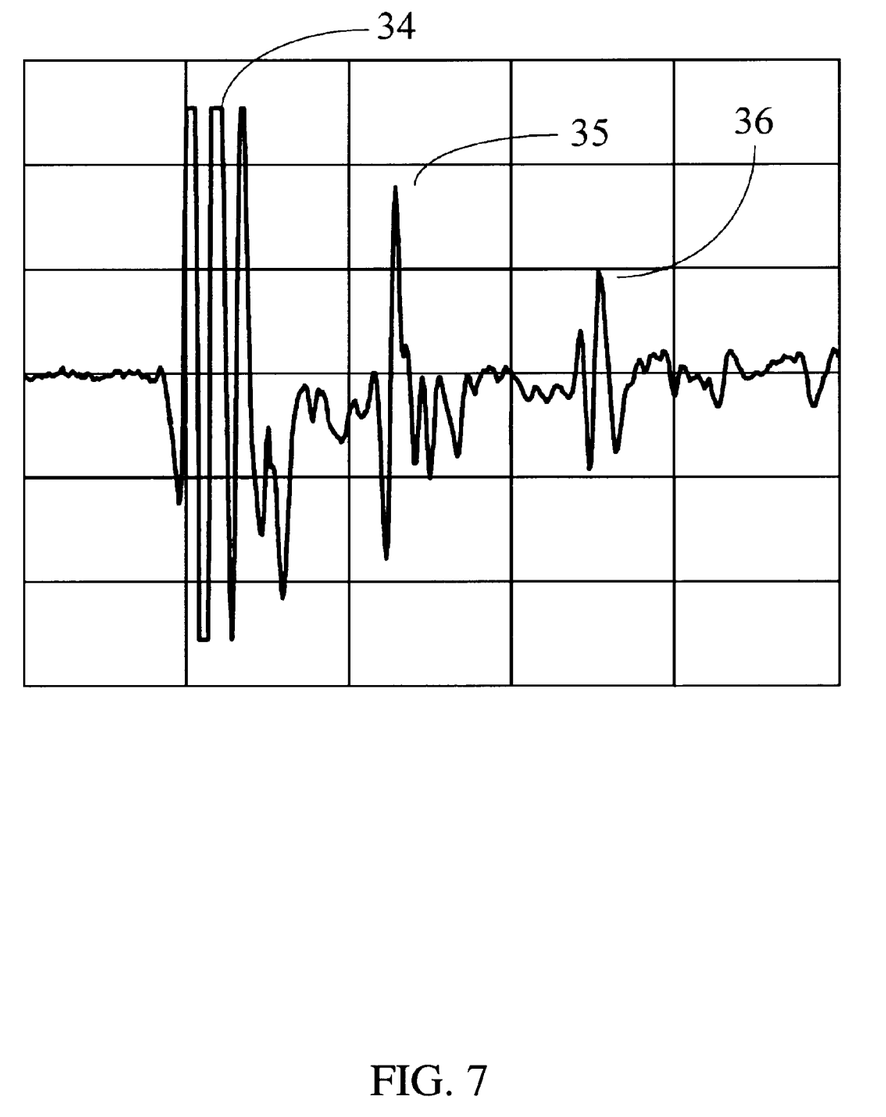
FIG. 7 is an oscilloscope trace of the received ultrasonic signals.

The signals obtained from the ultrasonic paths presented in FIG. 6 is shown in FIG. 7. The oscilloscope trace shown is a representative time domain signal response obtained from a section of HTS wire 1. The first reflection 34 is at the water/silver sheath surface 37 interface. The water/silver sheath reflection 34 may be used in the determination of the silver sheath thickness but the water/silver sheath reflection 34 is not the preferred signal to use. The undesirable characteristics of the water/silver sheath reflection include acoustic impedance, phase inversion and the fact that the water/silver and silver/core signals do not correlate, thus using the water/silver signal would be an unreliable signal to determine the thickness of the silver sheath.

The second 35 and third 36 signals shown in FIG. 7 are the first and second silver/core interface signals, which are the reflections at the silver/ceramic 38 interface. The second 35 and third 36 ultrasonic signal are processed using software on a digital computer 17 for the automatic determination of the time of flight and computation of silver sheath thickness for real-time monitoring during wire drawing. The calculation of the silver sheath thickness 39 is accomplished by determining the time elapsed between signals 35 and 36 interface echoes. The elapsed time determination represents the time for the ultrasonic energy 5 to travel through the silver sheath 31 twice. Therefore, the time is divided by two to calculate the time of flight through the silver sheath 31. This time of flight is then multiplied by the speed of sound in silver to obtain the silver sheath thickness 39 measurement. The silver sheath thickness measurement is displayed on a display device 41, preferably on a cathode ray tube display or liquid crystal display but other display means such as printer would be acceptable.

The ultrasonic velocity at this level of measurement precision in the silver sheath is not dependent on deformation energy levels usually encountered during the PIT processes. The ultrasonic velocity in the silver can be easily obtained from tables or from measurements made on representative silver tubes used for packing powder and subsequent drawing. [Nondestructive Testing Handbook, Volume Seven, Ultrasonic Testing, American Society of Nondestructive Testing, 1991]. The sensor is non destructive, rapid and is automated for real-time, continuous measurement of sheath thickness during HTS wire manufacturing.

Figure 8:
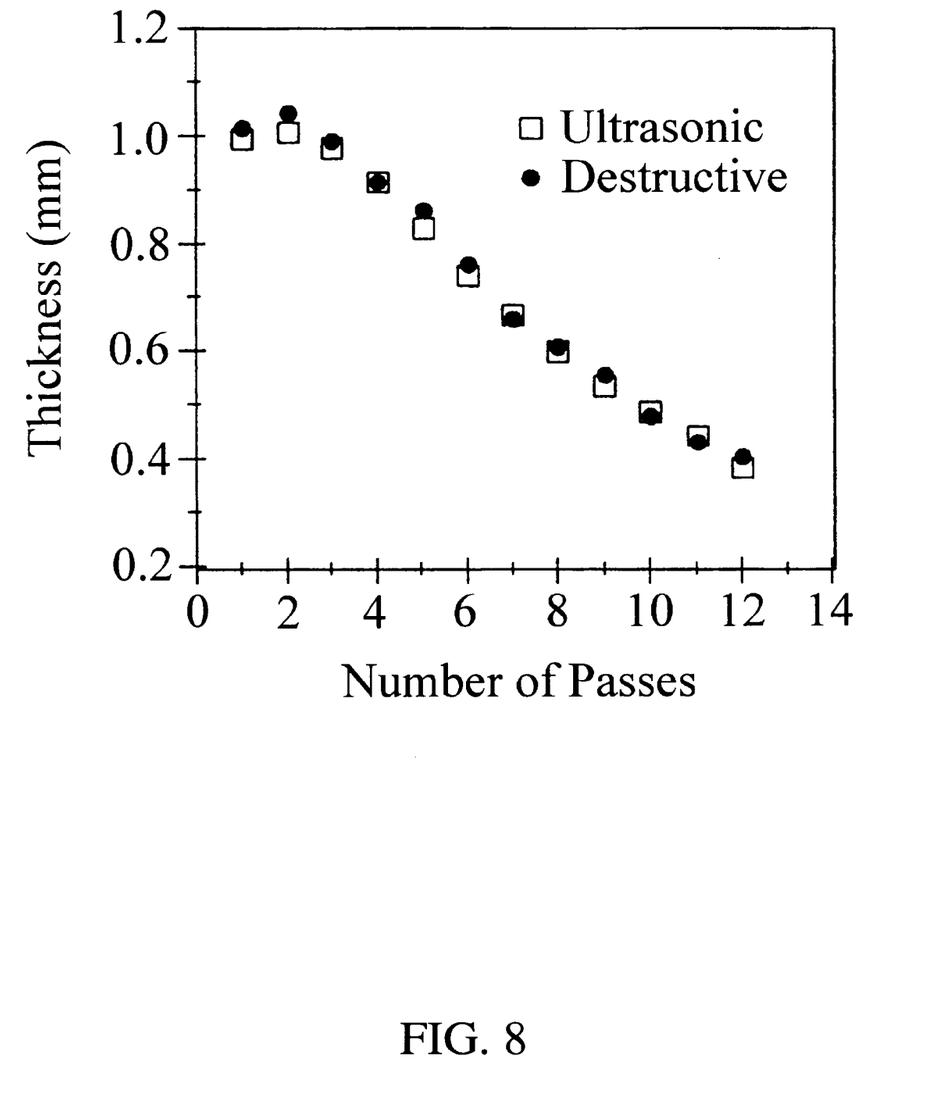
FIG. 8 is a comparison of ultrasonic and destructive measurements of silver sheath thickness.

Experimental silver sheath thickness 39 measurements using the new technique are shown in FIG. 8. Powder-In- Tube HTS wires were drawn using a gage value number 1AWG [American Wire Gage] (20.7% reduction in area) die set. FIG. 8 shows a plot of the silver sheath thickness (millimeters), as a function of the number of passes, measured by the ultrasonic method. Destructive measurements using metallographic techniques are also performed on the same set of samples to verify the ultrasonic measurements. The accuracy of measurements made using the newly developed ultrasonic method meets and exceeds those obtained by destructive metallographic methods.

what is claimed is:

1. An apparatus for the real-time non-destructive measuring of a thickness of a silver sheath surrounding a ceramic core of a high temperature superconductor (HTS) wire comprising:

a wire drawing fixture;

a remote pulser preamp producing a pulse energy;

an ultrasonic transducer acquiring the pulse energy, the ultrasonic transducer being mounted to the wire drawing fixture;

a squirter assembly attached to the ultrasonic transducer, the squirter assembly having a chamber being filled with a liquid and having at least one liquid jet hole for emitting a liquid stream, and the jet hole being functionally aligned with the wire being drawn through a drawing die;

the ultrasonic transducer producing a focused ultrasonic energy pulse, the focused ultrasonic energy pulse being transmitted via the liquid stream and directed at the wire;

the ultrasonic transducer receiving a reflected ultrasonic energy pulse and producing an ultrasonic energy signal;

a pulser/receiver acquiring the ultrasonic energy signal from the ultrasonic transducer and producing an amplified ultrasonic energy signal;

a digital oscilloscope acquiring the amplified ultrasonic energy signal from the pulser/receiver and producing a digital ultrasonic energy signal;

a digital computer acquiring the digital ultrasonic energy signal from the digital oscilloscope, the digital computer analyzing the digital signal to produce a silver sheath thickness measurement; and a display means for displaying the silver sheath thickness measurement.

2. The apparatus according to claim 1, further comprising:

an ultrasonic tube, the ultrasonic transducer being mounted in the ultrasonic tube and functionally aligned with the wire being drawn through a drawing die;

at least two mounting blocks;

at least one guide die;

the drawing die and the guide die being axially aligned and each being mounted to the mounting blocks, and the mounting blocks being attached to the wire drawing fixture; and an axial stage being mounted to a vertical stage and the vertical stage being mounted to an angular adjustment fixture whereby three degrees of freedom are provided the ultrasonic transducer.

3. The apparatus according to claim 2, wherein the drawing die and the guide die both have a same gauge value of 1AWG die set.

4. The apparatus according to claim 1, further comprising the pulser preamp supplying the pulse energy to the ultrasonic transducer, the pulser preamp also being supplied with a continuous power supply and being triggered by the pulser/receiver to supply the pulse energy.

5. The apparatus according to claim 1, wherein the ultrasonic transducer and squirter assembly are mounted perpendicular to the wire and horizontal to the wire drawing fixture, the ultrasonic transducer having a frequency of approximately 50 MHz.

6. The apparatus according to claim 1, wherein the ultrasonic energy signal further comprises a silver/water interface signal, a first silver/core interface signal, and a second silver/core interface signal.

7. The apparatus according to claim 1, wherein the digital computer acquires the digital ultrasonic energy signal from the digital oscilloscope via a general purpose interface bus.

8. The apparatus according to claim 1, wherein the digital computer performing the following steps:

determining an elapsed time between a first silver/core interface signal and a second silver/core interface signal resulting in an elapsed time determination;

dividing the elapsed time determination in half to produce a halved elapsed time; and multiplying the halved elapsed time by the speed of sound in silver to obtain the silver sheath thickness measurement.

9. A method for the real-time non-destructive measuring of a thickness of a silver sheath surrounding a ceramic core of a high temperature superconductor (HTS) wire comprising the following steps:

producing a pulse energy;

acquiring the pulse energy and producing a focused ultrasonic energy pulse;

drawing the wire through a path of the focused ultrasonic energy pulse;

producing a stream of liquid carrying the focused ultrasonic energy pulse, wherein the stream of liquid carrying the focused ultrasonic energy pulse is produced by a squirter assembly attached to an ultrasonic transducer, and the squirter assembly including a chamber being filled with the liquid and having at least one liquid jet hole functionally aligned with the wire being drawn through a drawing die;

directing the focused ultrasonic energy pulse at the wire;

acquiring a reflected ultrasonic energy pulse and producing an ultrasonic energy signal;

amplifying and exciting the ultrasonic energy signal to produce an amplified ultrasonic energy signal;

digitizing the amplified ultrasonic energy signal to produce a digital ultrasonic energy signal;

analyzing the digital ultrasonic energy signal to produce a silver sheath thickness reading; and displaying the silver sheath thickness reading.

10. The method according to claim 9, wherein the step of drawing the wire through the path of the ultrasonic energy pulse is performed by a wire drawing fixture comprising:

at least one drawing die and at least one guide die;

the drawing die and the guide die being axially aligned and each being mounted to a mounting block;

the mounting block being attached to the wire drawing fixture, the fixture also having at least one ultrasonic tube mounted to an axial stage, the axial stage being mounted to a vertical stage and the vertical stage being mounted to an angular adjustment fixture; and the ultrasonic transducer being mounted in the ultrasonic tube, the ultrasonic tube being functionally aligned with the wire being drawn through the drawing die.

11. The method according to claim 9, further including:

supplying the pulse energy to the ultrasonic transducer via a remote pulser preamp;

supplying a continuous power supply to the pulser preamp; and triggering the pulser preamp to supply the pulse energy.

12. The method according to claim 9, further comprising:

acquiring a water/silver interface signal;

acquiring a first silver/core interface signal; and acquiring a second silver/core interface signal.

13. The method according to claim 9, further comprising the step of transmitting the digital ultrasonic energy signal using a general purpose interface bus to an analyzing means for analyzing the digital ultrasonic energy signal.

14. The method according to claim 9, further comprising the steps of:

determining an elapsed time between a first silver/core interface signal and a second silver/core interface signal resulting in an elapsed time determination;

dividing the elapsed time determination in half to produce a halved elapsed time; and multiplying the halved elapsed time by the speed of sound in silver to obtain the silver sheath thickness measurement.

15. An apparatus for the non-destructive measuring of a thickness of a silver sheath surrounding a ceramic core of a high temperature superconductor (HTS) wire comprising:

means for producing a pulse energy;

means for acquiring the pulse energy and producing a focused ultrasonic energy pulse;

means for drawing the wire through a path of the focused ultrasonic energy pulse;

a squirter assembly means attached to an ultrasonic transducer for producing a stream of liquid carrying the focused ultrasonic energy pulse, wherein the squirter assembly means comprising a chamber being filled with a liquid and having at least one liquid jet hole functionally aligned with the wire whereby the stream of liquid carrying the focused ultrasonic energy pulse is directed at the wire;

means for acquiring a reflected ultrasonic energy and producing an ultrasonic energy signal;

means for amplifying and exciting an acquired ultrasonic energy signal to produce an amplified ultrasonic energy signal;

means for digitizing the amplified ultrasonic energy signal to produce a digital ultrasonic energy signal;

an analyzing means for analyzing the digital ultrasonic energy signal to produce a silver sheath thickness reading; and means for displaying the silver sheath thickness reading.

16. The apparatus according to claim 15, wherein the means for drawing the wire is a wire drawing fixture comprising:

the ultrasonic transducer;

at least one drawing die and at least one guide die;

an ultrasonic tube, the ultrasonic transducer being mounted in the ultrasonic tube and functionally aligned with the wire being drawn through the drawing die;

at least two mounting blocks;

the drawing die and the guide die being axially aligned and each being mounted to the mounting blocks, and the mounting blocks being attached to the wire drawing fixture; and an axial stage being mounted to a vertical stage and the vertical stage being mounted to an angular adjustment fixture whereby three degrees of freedom are provided the ultrasonic transducer.

17. The apparatus according to claim 16, wherein the ultrasonic transducer and a squirter assembly being mounted horizontally to the wire, the ultrasonic transducer having a frequency of approximately 50 MHz.

18. The apparatus according to claim 16, wherein the drawing die and the guide die both have a gage value of 1AWG die set.

19. The apparatus according to claim 15, wherein the means for producing the pulse energy is a pulser preamp, the pulser preamp also supplying the pulse energy to the ultrasonic transducer, the pulser preamp also being supplied with a continuous power supply and being triggered by a pulser/receiver to supply the pulse energy.

20. The apparatus according to claim 15, wherein the reflected ultrasonic energy is comprised of a silver/water interface signal, a first silver/core interface signal, and a second silver/core interface signal.

21. The apparatus according to claim 15, wherein the means for analyzing the digital ultrasonic energy signal is a digital computer, the digital computer acquiring the digital ultrasonic energy signal via a general purpose interface bus.

22. The apparatus according to claim 15, wherein the analyzing means is a digital computer.

23. The apparatus of claim 22, wherein the digital computer performing the following steps:

determining an elapsed time between a first silver/core interface signal and a second silver/core interface signal resulting in an elapsed time determination;

dividing the elapsed time determination in half to produce a halved elapsed time; and multiplying the halved elapsed time by the speed of sound in silver to obtain a silver sheath thickness measurement.

* * * * *

UNITED STATES PATENT AND TRADEMARK OFFICE
Certificate

Patent No. 5,974,885                                                               Patented: November 2, 1999

On petition requesting issuance of a certificate for correction of inventorship pursuant to 35 U.S.C. 256, it has been found that the above identified patent, through error and without deceptive intent; improperly sets forth the inventorship.

Accordingly, it is hereby certified that the correct inventorship of this patent is: Sanjai Parthasarathi, Santa Clara, CA; Michael D. Aesoph, Johnstown, PA; Jan Kajuch, Winder, PA; and Williams J. Majer.

Signed and Sealed this Thirty-First Day of July, 2001.

HEZRON E. WILLIAMS
*Supervisory Patent Examiner*
Art Unit 2856

UNITED STATES PATENT AND TRADEMARK OFFICE
CERTIFICATE OF CORRECTION

PATENT NO. : 5,974,885 B1
DATED : November 2, 1999
INVENTOR(S) : Sanjai Parthasarathi et al.

It is certified that error appears in the above-identified patent and that said Letters Patent is hereby corrected as shown below:

<u>Title page,</u>
Item [76], Inventor, the name "Williams J. Majer" should read -- William J. Majer --.

Signed and Sealed this

Ninth Day of April, 2002

Attest:

Attesting Officer

JAMES E. ROGAN
Director of the United States Patent and Trademark Office